United States Patent [19]

Schmidt et al.

[11] 3,939,175

[45] Feb. 17, 1976

[54] HYDROXYPHENYLATED HYDANTOINS

[75] Inventors: Andreas Schmidt, Reinach, Switzerland; Janet B. Peterson, Yonkers; Martin Dexter, Briarcliff Manor, both of N.Y.

[73] Assignee: Ciba-Geigy Corporation, Ardsley, N.Y.

[22] Filed: May 14, 1974

[21] Appl. No.: 469,717

Related U.S. Application Data

[63] Continuation-in-part of Ser. No. 357,744, May 3, 1973, abandoned.

[52] U.S. Cl.... 260/309.5; 260/45.8 N; 260/247.5 R; 260/248 NS; 260/465 E
[51] Int. Cl.² ........................................ C07D 49/32
[58] Field of Search ................................. 260/309.5

[56] References Cited
UNITED STATES PATENTS

| | | | |
|---|---|---|---|
| 3,544,623 | 12/1970 | Hansen et al. | 260/309.5 X |
| 3,553,258 | 1/1971 | Kaiser et al. | 260/309.5 X |

OTHER PUBLICATIONS

Chem. Abstracts 75:141140f.

*Primary Examiner*—Ethel G. Love
*Attorney, Agent, or Firm*—Luther A. R. Hall

[57] ABSTRACT

New hydroxyphenylated hydantoins are useful as stabilizers for synthetic organic polymeric materials. The new hydroxyphenylated hydantoins may be additionally substituted in the 1,3 and/or 5 positions of the hydantoin ring.

The hydroxyphenylated and 5-substituted hydroxyphenylated hydantoins are generally prepared by reacting hydroxyphenylated ketones or aldehydes with alkali cyanide and ammonium carbonate. Hydroxyphenylated hydantoins substituted in the 1 and/or 3 positions are generally prepared by reacting the 1 and/or 3-unsubstituted hydroxyphenylated hydantoins with the corresponding halogen or dialkylaminomethyl derivatives.

8 Claims, No Drawings

HYDROXYPHENYLATED HYDANTOINS

This application is a continuation-in-part of copending application, Serial No. 357,744, filed May 7, 1973, now abandoned.

The present invention relates to new compounds, the method for their manufacture, their use for stabilising organic material and the organic material stabilised with their aid.

The new compounds correspond to the general formula I

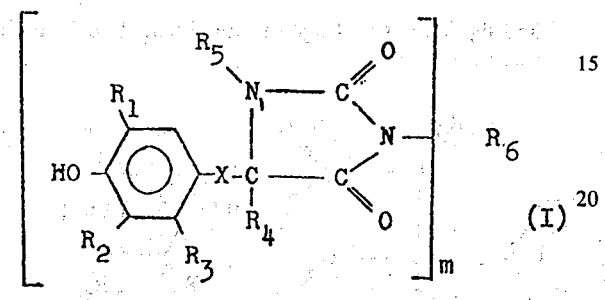

wherein $R_1$ denotes alkyl with 1 to 8 carbon atoms, cycloalkyl with 6 to 8 carbon atoms or aralkyl with 7 to 9 carbon atoms; $R_2$ denotes hydrogen, alkyl with 1 to 8 carbon atoms, cycloalkyl with 6 to 8 carbon atoms or aralkyl with 7 to 9 carbon atoms; $R_3$ denotes hydrogen or methyl; X denotes a direct bond, alkylene with 1 to 18 carbon atoms, which can be interrupted by oxygen or sulphur atoms, or the radical —O—CH$_2$—, wherein the oxygen atom is bonded to the phenol radical; $R_4$ denotes hydrogen, alkyl with 1 to 17 carbon atoms, alkenyl with 2 to 17 carbon atoms, thiaalkyl with 3 to 21 carbon atoms, oxaalkyl with 3 to 21 carbon atoms, cyclohexyl, benzyl, phenyl, alkylphenyl with 7 to 14 carbon atoms, alkoxyphenyl with 7 to 24 carbon atoms, chlorophenyl, dichlorophenyl, naphthyl or a group

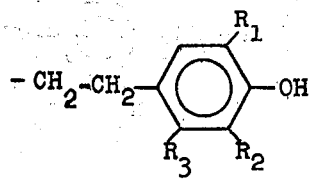

or X and $R_4$ conjointly with the carbon atom in the 5-position of the hydantoin ring denote one of the radicals

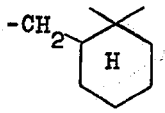 or 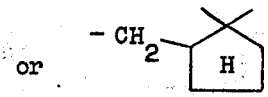 ;

$R_5$ denotes hydrogen, alkyl with 1 to 18 carbon atoms, alkenyl with 3 to 18 carbon atoms, cyclohexyl, benzyl or hydroxybenzyl which is unsubstituted or substituted by 1 to 3 alkyl groups each with 1 to 4 carbon atoms; $m$ denotes 1 to 3, $R_6$ — if $m$ is 1 — denotes hydrogen, alkyl with 1 to 18 carbon atoms, alkenyl with 3 to 18 carbon atoms, cyclohexyl, benzyl, hydroxybenzyl which is unsubstituted or substituted by 1 to 3 alkyl groups each with 1 to 4 carbon atoms, or one of the groups —CH$_2$CH$_2$CN or —(CH$_2$)$_q$—COOR$_7$, wherein $R_7$ is alkyl with 1 to 18 carbon atoms and $q$ is 1 or 2, or a group

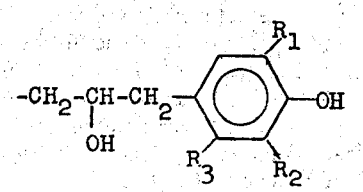

or — if $m$ is 2 — denotes alkylene with 1 to 18 carbon atoms, oxaalkylene with 4 to 21 carbon atoms, wherein the carbon atom bonded to the nitrogen does not carry any further hetero-atoms, thiaalkylene with 4 to 21 carbon atoms, wherein the carbon atom bonded to nitrogen carries no further hetero-atoms, or one of the groups

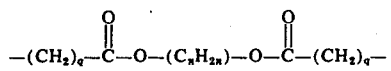

wherein $q$ is 1 or 2 and $n$ is 2 to 18,

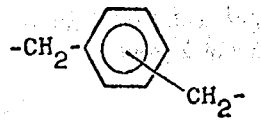

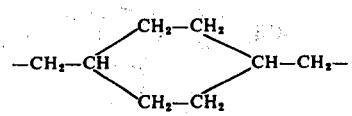

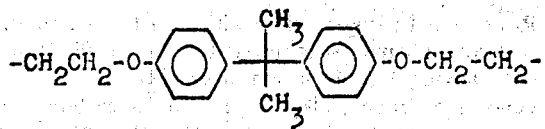

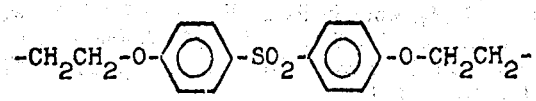

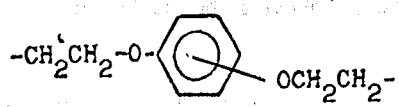

or — if $m$ is 3 — denotes alkanetriyl with 1 to 18 carbon atoms or the group

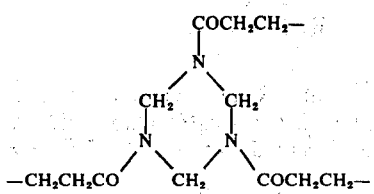

It has been found that the compounds of the formula I are very suitable for stabilising organic material against thermooxidative degradation. Herein, the new hydantoins of the formula I show, surprisingly, better activity than the ketones on which they are based.

Preferred compounds of the formula I are those wherein $R_1$ denotes alkyl with 1 to 4 carbon atoms or cycloalkyl with 6 to 8 carbon atoms; $R_2$ denotes hydrogen, alkyl with 1 to 5 carbon atoms or cycloalkyl with 6 to 8 carbon atoms; $R_3$ denotes hydrogen, X denotes one of the radicals —CH$_2$CH$_2$— or b)

$$-CH_2-\overset{\overset{\displaystyle CH_3}{\displaystyle |}}{CH}-;$$

$R_4$ denotes alkyl with 1 to 17 carbon atoms, cyclohexyl, benzyl, phenyl or a group

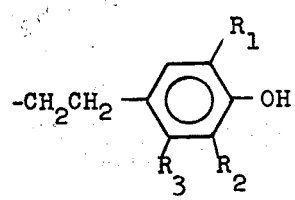

$R_5$ denotes hydrogen, alkyl with 1 to 18 carbon atoms or hydroxybenzyl substituted by 1 to 3 alkyl groups each having 1 to 4 carbon atoms; $R_6$ — if $m$ is 1 — denotes hydrogen, alkyl with 1 to 18 carbon atoms, hydroxybenzyl substituted by 1 to 3 alkyl groups each having 1 to 4 carbon atoms, or a group —(CH$_2$)$_q$—COOR$_7$, wherein $R_7$ is alkyl with 1 to 18 carbon atoms and $q$ is 1 or 2, or — if $m$ is 2 — denotes alkylene with 1 to 18 carbon atoms or the group —CH$_2$CH$_2$—O—CH$_2$CH$_2$—.

Amongst the preferred compounds the following classes should above all be mentioned:

a)

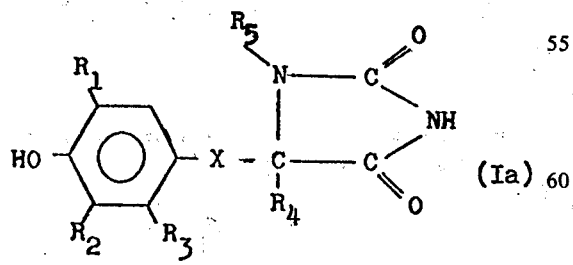 (Ia)

wherein $R_1$ and $R_2$ independently of one another denote alkyl with 1 to 4 carbon atoms, $R_3$ denotes hydrogen, X denotes a direct bond, —CH$_2$—CH$_2$— or

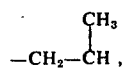

$R_4$ denotes alkyl with 1 to 17 carbon atoms, cyclohexyl, benzyl, phenyl or a group

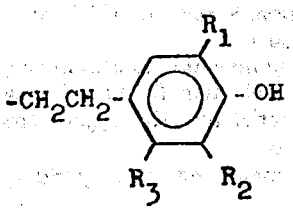

and $R_5$ denotes hydrogen or alkyl with 1 to 18 carbon atoms.

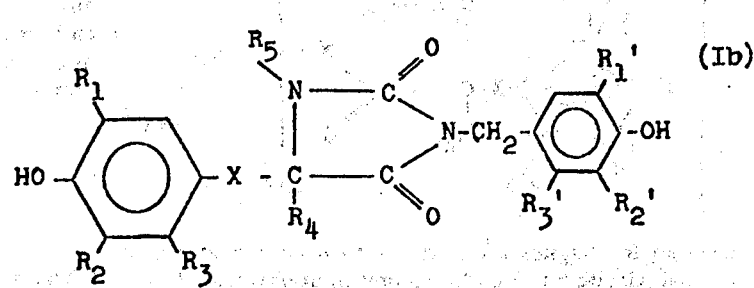 (Ib)

wherein $R_1$, $R_2$, $R_1'$ and $R_2'$ independently of one another denote alkyl with 1 to 4 carbon atoms, $R_3$ and $R_3'$ independently of one another denote hydrogen or methyl, X denotes a direct bond, —CH$_2$—CH$_2$— or $$-CH_2-\overset{\overset{\displaystyle CH_3}{\displaystyle |}}{CH}-,$$

$R_4$ denotes alkyl with 1 to 17 carbon atoms, cyclohexyl, benzyl, phenyl or a group

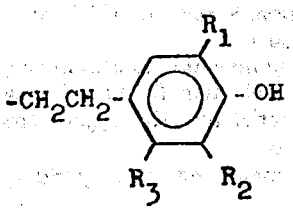

and $R_5$ denotes hydrogen, alkyl with 1 to 18 carbon atoms or hydroxybenzyl substituted by 1 to 3 alkyl groups each having 1 to 4 carbon atoms.

c)

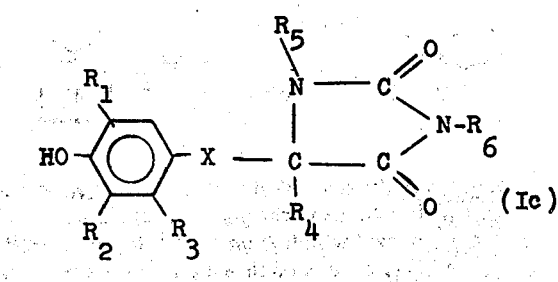 (Ic)

wherein $R_1$ and $R_2$ independently of one another denote alkyl with 1 to 4 carbon atoms, $R_3$ denotes hydrogen, X denotes a direct bond, —CH$_2$—CH$_2$— or

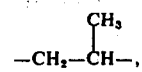

R₄ denotes alkyl with 1 to 17 carbon atoms or a group

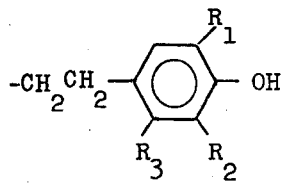

R₅ denotes hydrogen or alkyl with 1 to 18 carbon atoms and R₆ denotes alkyl with 1 to 18 carbon atoms.

d) 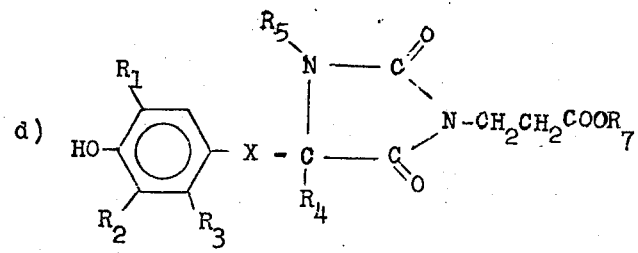

wherein R₁ and R₂ independently of one another denote alkyl with 1 to 4 carbon atoms, R₃ denotes hydrogen, X denotes a direct bond, —CH₂—CH₂— or

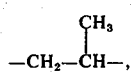

R₄ denotes alkyl with 1 to 17 carbon atoms or a group

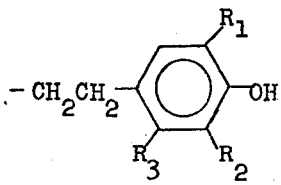

R₅ denotes hydrogen or alkyl with 1 to 18 carbon atoms and R₇ denotes alkyl with 1 to 18 carbon atoms.

e) 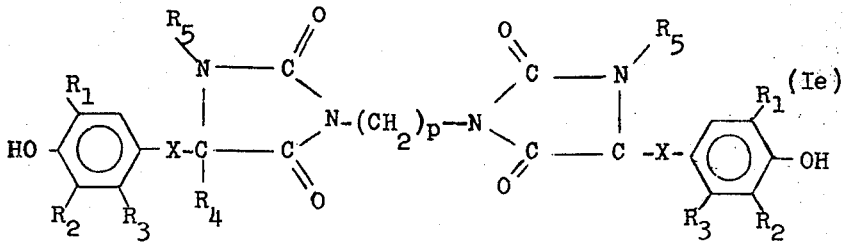

wherein R₁ and R₂ independently of one another denote alkyl with 1 to 4 carbon atoms, R₃ denotes hydrogen, X denotes a direct bond, —CH₂—CH₂— or

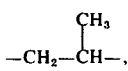

R₄ denotes alkyl with 1 to 17 carbon atoms or the group

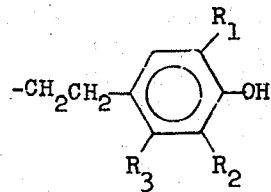

R₅ denotes hydrogen or alkyl with 1 to 18 carbon atoms an p denotes 1 to 18.

In the definition of the compounds of the formula I, R₁, R₂, R₃, R₅, R₆, and R₇ can represent alkyl groups. Within the indicated limits, theese groups can be methyl, ethyl, isopropyl, butyl, sec.-butyl, tert.-butyl, amyl, sec.-amyl, tert.-amyl, hexyl, heptyl, octyl, tert.-octyl, nonyl, decyl, undecyl, dodecyl, tetradecyl, hexadecyl or octadecyl.

R₁ and R₂ can also be cyclic alkyl groups with 6 to 8 carbon atoms. These are, for example, cyclohexyl, cycloheptyl or cyclooctyl. The preferred cyclic alkyl group is the 1-methylcyclohexyl-(1) group.

As aralkyl groups, R₁ and R₂ can denote, for example, benzyl or α-phenylethyl. R₄, R₅ and R₆ can denote alkenyl groups, for example, the allyl group. When R₄ denotes oxaalkyl it can be, for example, 3-oxabutyl, 2-oxapentyl, 2-oxaheptyl, or oxapentadecyl, whilst if it denotes thiaalkyl it can be, for example, 3-thiabutyl, 3-thiapentyl, 3-thiaheptyl, 3-thiaundecyl, 3-thiapentadecyl, 3-thianonadecyl or 3-thiaheneicosyl.

When R₄ denotes alkylphenyl, it can be, for example, o-tolyl, p-tert.-butylphenyl or p-tert.-octylphenyl.

When R₄ denotes alkoxyphenyl it can be, for example, o-methoxyphenyl, p-methoxyphenyl, p-octoxyphenyl, or p-octadecoxyphenyl.

If the radicals X and R₆ in the definition of the formula I are alkylene, it can be, for example, methylene, ethylene, 1,2-propylene, 1,3-propylene, tetramethylene, hexamethylene or octamethylene.

When R₆ is oxaalkylene it can denote, for example, the divalent radical of 2-oxapropane, 2-oxabutane, 3-oxapentane, 3-oxaheptane, 3-oxaundecane, 3-oxapentadecane or 3-oxaheneicosane, whilst as thiaalkylene it can denote the divalent radical of 3-thiapropane, 3-thiabutane, 3-thiapentane, 3-thiaheptane, 3-thiaundecane, 3-thiapentadecane, 3-thianonadecane, 3-thiaheneicosane or 4-thiadecane.

When $R_6$ denotes alkanetriyl it can be, for example, neopentanetriyl.

Examples of compounds of the formula I are: 5-(3',5'-diisopropyl-4'-hydroxy-phenylethyl)-5-methyl-hydantoin, 5-(3',5'-di-tert.-butyl-4'-hydroxybenzyl)-5-heptadecylhydantoin, 5-[(3',5'-di-tert.-butyl-4'-hydroxybenzylmercapto)-methyl]-5-heptadecyl-hydantoin, 5-[(3',5'-di-tert.-butyl-4'-hydroxyphenoxy)-methyl]-5-dodecyl-hydantoin, 5-(3'-tert.-butyl-4'-hydroxy-5',6'-dimethyl-phenylethyl)-5-methylhydantoin, 5-(3'-tert.-butyl-4'-hydroxy-5'-methyl-phenylethyl)-5-vinyl-hydantoin, 5-(3',5'-di-tert.-butyl-4'-hydroxy-phenylethyl)-5-(3-thiaheptyl)-hydantoin, 5-(3',5'-di-tert.-butyl-4'-hydroxy-phenylethyl)-5-cyclohexyl-hydantoin, 5-(3',5'-di-tert.-butyl-4'-hydroxy-phenylethyl)-5-(p-tert.-butylphenyl)-hydantoin, 3-allyl-5-(3',5'-di-tert.-butyl-4'-hydroxy-phenylethyl)-5-methyl-hydantoin, 3-cyclohexyl-5-(3',5'-di-tert.-butyl-4'-hydroxyphenylethyl)-5-methyl-hydantoin, 3-benzyl-5-(3',5'-di-tert.-butyl-4'-hydroxy-phenylethyl)-5-methyl-hydantoin and 3,3'-tetramethylene-bis-[5-(3'',5''-di-tert.-butyl-4''-hydroxy-phenylethyl)-5-methyl-hydantoin].

The compounds of the formula I in which $R_6$ has a different meaning from hydrogen may be prepared from compounds of the formula I in which $m$ denotes 1 and $R_6$ denotes hydrogen (here described as compounds of the formula II).

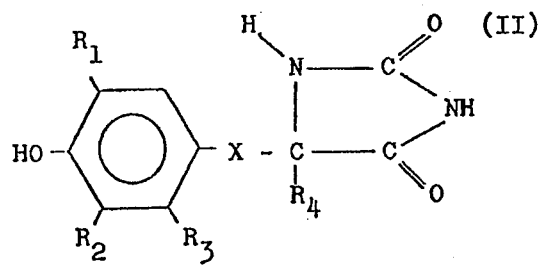

Such compounds may be prepared, in turn, by reaction of 1 mol of a compound of the formula III

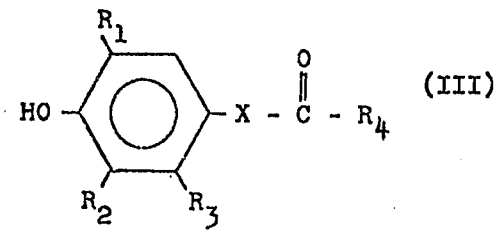

with one mol of sodium cyanide or potassium cyanide and an excess of ammonium carbonate in a polar solvent at 40°–50°C.

A typical example of a compound of formula III is 3,5-di-tert-butyl-4-hydroxyphenylethyl methyl ketone made by the teachings of U.S. Pat. No. 3,266,443.

Methanol, ethanol, isopropanol, dimethylformamide or dioxane can be used as solvents, their mixtures with water being employed preferentially.

Compounds of the formula I in which $R_6$ denotes a hydroxybenzyl group substituted by 1–3 alkyl groups each with 1 to 4 carbon atoms may be prepared by reaction of the compounds of the formula II with compounds of the formula IV

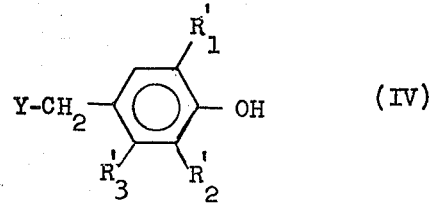

wherein Y denotes a halogen atom, the group

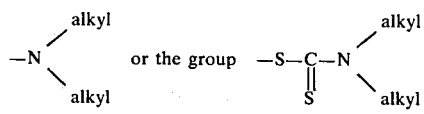

The intermediate (3,5-di-tert-butyl-4-hydroxybenzyl)-dimethylamine is commercially available and useful in the synthesis of many compounds of this invention.

The reaction is preferably carried out in the presence of a basic catalyst such as sodium methylate, sodium hydride, calcium hydride, lithium amide or sodium amide. Hydrocarbons, ethers, alcohols and, preferably, dimethylformamide or dimethylacetamide can be used as solvents.

Compounds of the formula I in which $R_6$ denotes alkyl, alkenyl, cyclohexyl, benzyl or —CH$_2$—COOR$_7$ may be preferably prepared by reaction of the compounds of the formula II with compounds of the formula V

$$Z-R_6 \quad (V)$$

wherein Z denotes a halogen atom.

The reaction is carried out in the presence of a basic catalyst such as potassium carbonate, sodium hydroxide, sodium methylate or lithium amide. As solvents, it is possible to use alcohols such as methanol, ethanol, isopropanol or butanol, ethers such as tetrahydrofurane or dioxane, ketones such as acetone, methyl ethyl ketone or cyclohexanone, as well as dimethylformamide or dimethylacetamide.

The compounds of the formula I, in which $R_6$ denotes one of the groups —CH$_2$CH$_2$CN or —CH$_2$CH$_2$—COOR$_7$, may be prepared by reaction of the compounds of the formula II with acrylonitrile or compounds of the formula VI, respectively

$$CH_2=CH-COOR_7 \quad (VI)$$

The reaction takes place in the presence of a basic catalyst such as sodium methylate, sodium hydride, calcium hydride, lithium amide or sodium amide. Alcohols, ethers, ketones or dimethylformamide or dimethylacetamide can be used as solvents.

The compounds of the formula I in which $R_6$ denotes the group

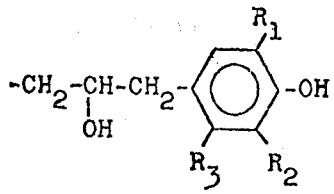

may be prepared by reaction of the compounds of the formula II with compounds of the formula VII

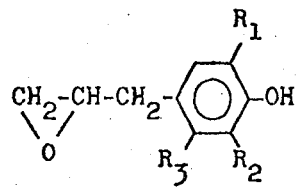 (VII)

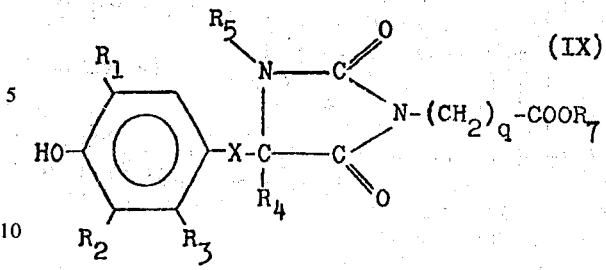 (IX)

The reaction takes place in the presence of a basic catalyst, preferably a tertiary amine such as triethylamine, tripropylamine or pyridine, in a polar solvent, for example dioxane, tetrahydrofurane, isopropanol or dimethylformamide.

Compounds of the formula I in which m is 2 and $R_6$ denotes alkylene, oxaalkylene, thiaalkylene or one of the groups

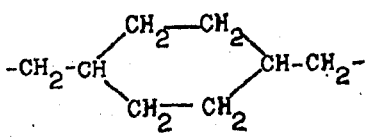

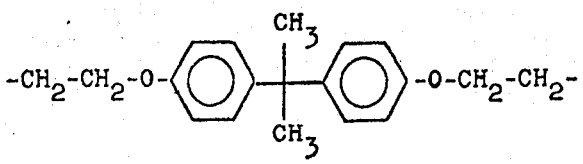

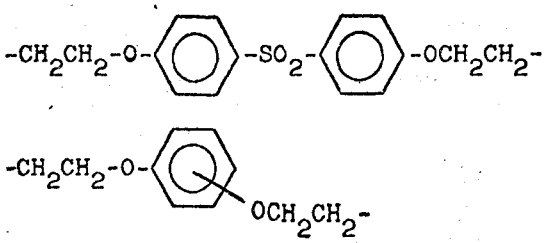

may be prepared by reaction of the compounds of the formula II with dihalides of the formula VIII $Z-R_6-Z$ (VIII)

wherein Z denotes a halogen atom. The reaction takes place in the presence of a basic catalyst such as potassium carbonate, sodium hydroxide, sodium methylate or lithium amide. As solvents it is possible to use alcohols such as methanol, ethanol, isopropanol or butanol, ethers such as tetrahydrofurane or dioxane, ketones such as acetone, methyl ethyl ketone or cyclohexanone, as well as dimethylformamide or dimethylacetamide.

Compounds of the formula I in which m is 2 and $R_6$ denotes the group

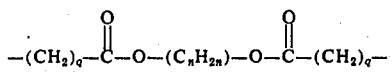

may be obtained by reaction of a compound of the formula IX with a diol of the formula X $HO-(C_nH_{2n})-OH$ (X)

The reaction takes place according to a method customary for trans-esterification reactions, in the presence of an acid catalyst such as hydrochloric acid, sulphuric acid or p-toluenesulphonic acid or of a basic catalyst such as lithium hydroxide, sodium hydride or potassium amide.

Compounds of the formula I in which m is 3 and $R_6$ denotes alkanetriyl may be prepared by reaction of the compounds of the formula II with compounds of the formula XI

 (XI)

wherein Z denotes a halogen atom. The reaction take place under the conditions described for the reaction with the compounds V and VIII.

Compounds of formula I in which both $R_6$ and $R_5$ have a different meaning from hydrogen may be prepared by the reaction of compounds of formula XII

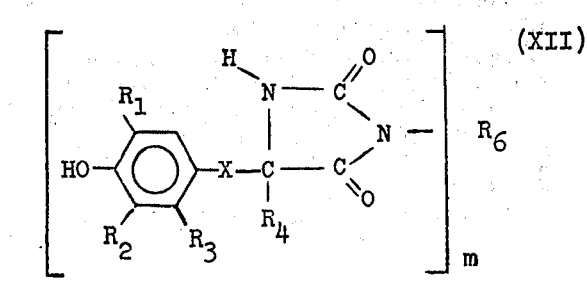 (XII)

with compounds of formula IV or V under the conditions described for the reaction of compounds II with IV or V.

Compounds of formula I in which $R_6$ is hydrogen and $R_5$ has a different meaning from hydrogen may be prepared by the reaction of compounds of formula II in a three step synthesis first with a secondary amine and formaldehyde to give compounds of formula XIII

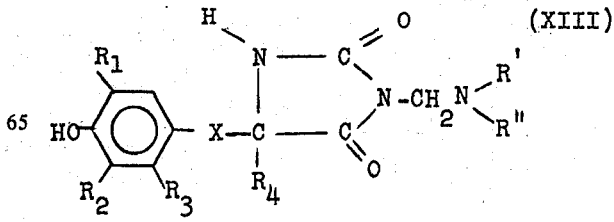 (XIII)

The preferred secondary amines are morpholine and piperidine where R' and R" together are —CH$_2$CH$_2$OCH$_2$CH$_2$— and —(CH$_2$)$_5$—.

Compounds of formula XIII may then be reacted with compounds of formula XIV

wherein R$_5$ has a meaning other than hydrogen and Z denotes a halogen atom under the conditions described for the reaction of compounds II with V to yield compounds of formula XV.

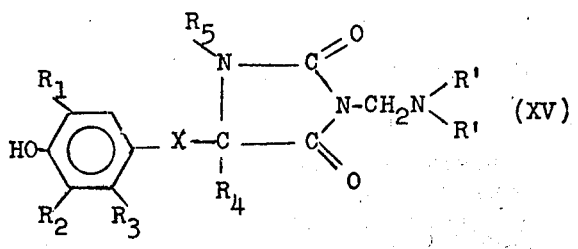

Finally compounds of formula XV may be hydrolyzed under either acid or alkaline conditions to remove the 3-aminomethyl group to give the desired 1-R$_5$-5-hydroxyphenylated hydantoin of formula I$a$

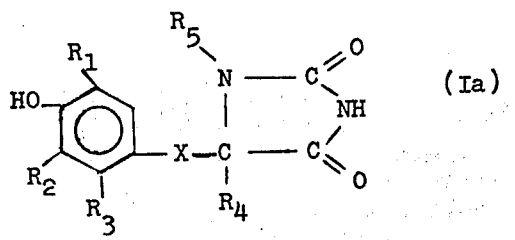

Hydrolysis of XV to I$a$ is done under mild conditions using alkali such as aqueous sodium hydroxide or aqueous potassium hydroxide or with aqueous acid such as hydrochloric acid or sulfuric acid.

Compounds of formula I in which R$_6$ is hydrogen and R$_5$ has a different meaning from hydrogen may also be prepared by the reaction of a hydroxyphenylated ketone of formula III with a primary amine of the formula XVI

and potassium cyanide in glacial acetic acid to give an aminonitrile of formula XVII

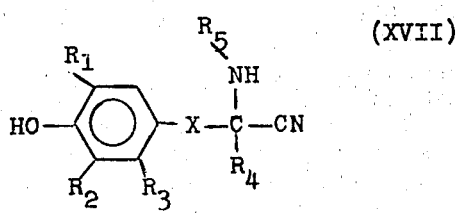

The compounds of formula XVII may be reacted with potassium cyanate in acid solution to prepare compounds of formula I$a$.

Compounds of general formula I in which both R$_5$ and R$_6$ have a different meaning from hydrogen may be prepared by the reaction of compounds of formula I$a$ with compounds of formula IV, V, VI or VIII under conditions described for the reaction of compounds of formula II with compounds of formula IV, V, VI or VIII.

The compounds of the formula I are used as stabilisers for organic substrates. Examples of such substrates are:

1. Polymers which are derived from singly or doubly unsaturated hydrocarbons, such as polyolefins, such as, for example, polyethylene, which can optionally be crosslinked, polypropylene, polyisobutylene, polymethylbutene-1, polymethylpentene-1, polybutene-1, polyisoprene, polybutadiene, polystyrene, copolymers of the monomers on which the homopolymers mentioned are based, such as ethylenepropylene copolymers, propylene-butene-1 copolymers, propylene-isobutylene copolymers, and styrene-butadiene copolymers, as well as terpolymers of ethylene and propylene with a diene, such as, for example, hexadiene, dicyclopentadiene or ethylidenenorbornene; mixtures of the above mentioned homopolymers such as, for example, mixtures of polypropylene and polyethylene, polypropylene and polybutene-1, polypropylene and polyisobutylene.

2. Vinyl polymers containing halogen, such as polyvinyl chloride, polyvinylidene chloride, and polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals such as polyoxymethylene and polyoxyethylene, as well as those polyoxymethylenes which contain ethylene oxide as the comonomer.

7. Polyphenylene oxides.
8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.
12. Polyesters which are derived from dicarboxylic acids and dialcohols, and/or from hydroxycarboxylic acids or the corresponding lactones, such as polyethylene glycol terephthalate and poly-1,4-dimethylolcyclohexane terephthalate.
13. Crosslinked polymers which are derived from aldehydes on the one hand and phenols, ureas and melamines on the other, such as phenol-formaldehyde, urea-formaldehyde and melamine-formaldehyde resins.
14. Alkyd resins, such as glycerine-phthalic acid resins and their mixtures with melamine-formaldehyde resins.
15. Unsaturated polyester resins which are derived from copolyesters of saturated and unsaturated dicarboxylic acids with polyhydric alcohols, as well as vinyl compounds as crosslinking agents, and also their halogen-containing modifications of low inflammability.

16. Natural polymers, such as cellulose, rubber, proteins, and their polymer-homologously chemically modified derivatives, such as cellulose acetates, cellulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The compounds of the formula I are incorporated into the substrates in a concentration of 0.01 to 5% by weight calculated relative to the material to be stabilised.

Preferably, 0.05 to 2.0, especially preferentially 0.1 to 1.0% by weight of the compounds, calculated relative to the material to be stabilised, are incorporated into the latter. The incorporation can, for example, be effected by admixing at least one of the compounds of the formula I and optionally further additives according to the methods customary in the art, before or during shaping, or by application of the dissolved or dispersed compounds onto the polymer, if appropriate with subsequent evaporation of the solvent.

In the case of crosslinked polyethylene, the compounds are added before the crosslinking.

As further additives, together with which the stabilisers can be employed, there should be mentioned:

A. Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

B. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole and tris(3,5-di-tert.-butyl-4-hydroxyphenyl)-phosphite.

C. Hydroxylated thiodiphenyl ethers, such as, for example, 2,2'-thiobis-(6-tert.-butyl-4-methylphenol), 2,2'-thiobis-(4-octylphenol), 4,4'-thiobis-(6-tert.-butyl-3-methylphenol), 4,4'-thiobis-(3,6-di-sec.-amylphenol) and 4,4'-thiobis-(6-tert.-butyl-2-methylphenol).

D. Alkylidene-bis-phenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol, 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(α-methylcyclohexyl)-phenyl], 1,1-bis-(3,5-dimethyl-2-hydroxyphenylbutane), 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecyl-mercapto-butane, 1,1,5,5-tetra-(5-tert.-butyl-4-hydroxy-2-methylphenyl)-pentane and ethylene glycol-bis-[3,3-bis-(3'-tert.-butyl-4'-hydroxyphenyl)-butyrate].

E. O-, N- and S-benzyl compounds, such as, for example, 3,5,3',5'-tetra-tert.-butyl-4,4'-dihydroxydibenzyl-ether, 4-hydroxy-3,5-dimethylbenzyl-mercaptoacetic acid octadecyl ester, tri-(3,5-di-tert.-butyl-4-hydroxybenzyl)-amine, and the bis-(4-tert.-butyl-3-hydroxy-2,6-dimethylbenzyl)-dithiolterephthalate.

F. Hydroxybenzylated malonic esters, such as, for example, 2,2-bis-(3,5-di-tert.-butyl-2-hydroxybenzyl)-malonic acid dioctadecyl ester, 2-(3-tert.-butyl-4-hydroxy-5-methylbenzyl)-malonic acid dioctydecyl ester, 2,2-bis-(3,5-di-tert.-butyl-4-hydroxybenzyl)-malonic acid didodecylmercapto-ethyl ester, and 2,2-bis-(3,5-di-tert.-butyl-4-hydroxybenzyl)-malonic acid di-(4-tert.-octylphenyl) ester.

G. Hydroxybenzyl-aromatics, such as, for example, 1,3,5-tri(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

H. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)-isocyanurate.

I. Amides of 3,5-di-tert.-butyl-4-hydroxyphenyl-propionic acid, such as, for example 1,3,3-tri-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine.

K. Esters of 3,5-di-tert.-butyl-4-hydroxyphenyl-propionic acid with monohydric or polyhydric alcohols, such as, for example, methanol, ethanol octadecanol; 1,6-hexanediol; 1,9-nonanediol, ethylene glycol; 1,2-propanediol, diethylene glycol, thiodiethylene glycol, neopentyl glycol, 3-thiaundecanol, 3-thia-pentadecanol, trimethylhexanediol, trimethylolethane, trimethylolpropane, tris-hydroxyethyl-isocyanurate, 4-hydroxymethyl-1-phospha-2,6,7-trioxabicyclo [2,2,2]-octane and pentaerythritol.

L. Esters of 5-tert.-butyl-4-hydroxy-3-methylphenyl-propionic acid with monohydric or polyhydric alcohols, such as, for example methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]-octane.

M. Esters of 3,5-di-tert.-butyl-4-hydroxyphenylacetic acid with monohydric or polyhydric alcohols, such as, for example methanol, ethanol, octadecanol, 1,6-hexanediol; 1,9-nonanediol, ethylene glycol, 1,2-propanediol, diethylene glycol, thiodiethylene glycol, neopentyl glycol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]-octane.

N. Acylaminophenols, such as, for example, N-(3,5-di-tert.-butyl-4-hydroxyphenyl)-stearic acid amide and N,N'-di-(3,5-di-tert.-butyl-4-hydroxyphenyl)-thio-bis-acetamide.

0. Benzylphosphonates, such as, for example, 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzylphosphonic acid dioctadecyl ester.

Amongst the aminoaryl derivatives there should be mentioned aniline and naphthylamine derivatives as well as their heterocyclic derivatives, for example: phenyl-1-naphthylamine, phenyl-2-naphthylamine, N,N'-diphenyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline,
mono- and di-octyliminodibenzyl and polymerised 2,2,4-trimethyl-1,2-dihydroquinoline.

2. UV-absorbers and light protection agents such as:
a. 2-(2'-Hydroxyphenyl)-benztriazoles, for example the 5'-methyl-, 3',5'-di-tert.-butyl-, 5'-tert.-butyl-, 5-chloro-3'-, 5'-tert.-butyl-, 5-chloro-3'-tert.-butyl-5'-methyl, 3'-sec.-butyl-5'-tert.-butyl-, 3'-[α-methylbenzyl]-5'-methyl-, 3'-[α-methylbenzyl]-5'-methyl-5-chloro, 4'-octoxy-, 3',5'-di-tert.-amyl-, 3'-methyl-5'-carbomethoxyethyl-, and 5-chloro-3',5'-di-tert.-amyl-derivative.
b. 2,4-bis-(2'-Hydroxyphenyl)-6-alkyl-s-triazines, for example the 6-ethyl- or 6-undecyl-derivative.
c. 2-Hydroxy-benzophenones, for example the 4-hydroxy-, 4-methoxy-, 4-octoxy-, 4-decyloxy-, 4-dodecyloxy-, 4,2',4'-trihydroxy- or 2'-hydroxy-4,4'-dimethoxy-derivative.
d. 1,3-bis-(2'-Hydroxy-benzoyl)-benzenes, for example 1,3-bis-(2'-hydroxy-4'-hexyloxy-benzoyl)-benzene, 1,3-bis-(2'-hydroxy-4'-octoxy-benzoyl)-benzene, and 1,3-bis-(2'-hydroxy-4'-dodecyloxy-benzoyl)-benzene.
e. Aryl esters of optionally substituted benzoic acids such as, for example, phenyl salicylate, octylphenyl salicylate, di-benzoylresorcinol, bis-(4-tert.-butylbenzoyl)-resorcinol, benzoxyl-resorcinol, 3,5-di-tert.-butyl-4-hydroxybenzoic acid 2,4-di-tert.-butylphenyl ester, octadecyl ester or 2-methyl-4,6-di-tert.-butylphenyl ester.
f. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.
g. Nickel compounds, for example nickel complexes of 2,2'-thio-bis-(4-tert.-octylphenol), such as the 1:1 and 1:2 complex, optionally with other ligands such as n-butylamine, nickel complexes of bis-(4-tert.-octylphenyl)-sulphone, such as the 2:1 complex, optionally with other ligands such as 2-ethyl-caproic acid, nickel dibutyldithiocarbamate, nickel salts of 4-hydroxy-3,5-di-tert.-butylbenzyl-phosphonic acid monoalkyl esters, such as the methyl, ethyl or butyl ester, the nickel complex of 2-hydroxy-4-methyl-phenyl-undecylketonoxime and nickel 3,5-di-tert.-butyl-4-hydroxy-benzoate.
h. Oxalic acid diamides, for example 4,4'-di-octyloxyanilide, 2,2'-di-octyloxy-5,5'-di-tert.-butyl-oxanilide, and 2,2'-di-dodecyloxy-5,5'-di-tert.-butyl-oxanilide.
i. Sterically hindered amines, for example 4-benzoyloxy-2,2,6,6-tetramethylpiperidine, 4-stearoyloxy-2,2,6,6-tetramethylpiperidine, bis-(2,2,6,6-tetramethylpiperidyl)-sebacate, 3-n-octyl-7,7,9,9-tetramethyl-1,3,8-triaza-spiro [4,5]-decan-2,4-dione.

3. Metal deactivators, such as oxanilide, isophthalic acid dihydrazide, sebacic acid bis-phenylhydrazide, bis-benzylideneoxalic acid dihydrazide, N,N'-diacetyl-adipic acid dihydrazide, N,N'-bis-salicyloyl-oxalic acid dihydrazide and N,N'-bis-salicyloyl-hydrazine.

4. Phosphites, such as triphenylphosphite, diphenyl-alkyl-phosphites, phenyldialkylphosphites, trinonylphenylphosphite, trilaurylphosphite, trioctadecylphosphite, 3,9-di-isodecyloxy-2,4,8,10-tetraoxa-3,9-diphospha-spiro-(5,5)undecane and tri-(4-hydroxy-3,5-di-tert.-butylphenyl)-phosphite.

5. Compounds which destroy peroxide, such as esters of β-thiodipropionic acid, for example the lauryl, stearyl, myrystyl or tridecyl ester, salts of 2-mercaptobenzimidazole, for example the zinc salt, and diphenylthiourea for polyolefines.

6. Polyamide stabilisers such as copper salts in combination with iodides and/or further phosphorus compounds and salts of divalent manganese.

7. Basic co-stabilisers, such as polyvinylpyrrolidone, melamine, benzoguanamine, triallyl cyanurate, dicyandiamide, urea derivatives, hydrazine derivatives, amines, polyamides, polyurethanes, and alkali metal salts and alkaline earth metal salts of higher saturated or unsaturated fatty acids such as, for example, Ca stearate.

8. PVC stabilisers, such as organic tin compounds, organic lead compounds and Ba/Cd salts of fatty acids.

9. Nucleating agents, such as 4-tert.-butylbenzoic acid, adipic acid and diphenylacetic acid.

10. Other additives such as plasticisers, lubricants, for example glycerine monostearate, emulsifiers, antistatic agents, flameproofing agents, pigments, carbon black, asbestos, glass fibres, kaolin and talc.

The invention is explained in more detail in the examples which follow. Herein, per cent (%) denotes per cent by weight and parts denote parts by weight.

EXAMPLE 1

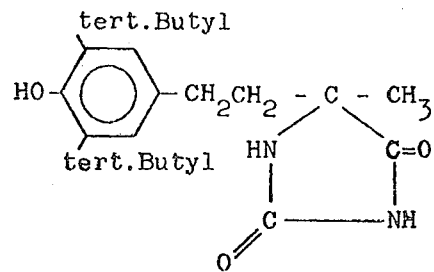

27.6 g (0.1 mol) of 3,5-di-tert.-butyl-4-hydroxy-phenylethyl methyl ketone, 4.9 g (0.1 mol) of sodium cyanide and 28.8 g (0.3 mol) of ammonium carbonate are initially introduced into 180 ml of 80% strength aqueous ethanol and the mixture is heated to 45°C for 6 hours whilst stirring. Thereafter it is diluted with 60 ml of water and cooled to room temperature over the course of 2 hours. The precipitate formed is filtered off, thoroughly washed first with water and then with hexane and recrystallised from acetonitrile. 31.5 g of 5-(3',5'-di-tert.-butyl-4'-hydroxy-phenylethyl)-5-methyl-hydantoin (stabiliser No. 1) of melting point 207°–209°C are thus obtained.

EXAMPLE 2

If, in Example 1, 3,5-di-tert.-butyl-4-hydroxy-phenylethyl methyl ketone is replaced by an equivalent amount of (3-tert.-butyl-4-hydroxy-5-methyl-phenylethyl methyl ketone and otherwise the same procedure is followed, 5-(3'-tert.-butyl-4'-hydroxy-5'-methyl-phenylethyl)-5-methylhydantoin of melting point 210°–211°C is obtained (stabiliser No. 2).

EXAMPLE 3

If, in Example 1, 3,5-di-tert.-butyl-4-hydroxyphenylethyl methyl ketone is replaced by an equivalent amount of 2-(3,5-di-tert.-butyl-4'-hydroxy-phenyl)-isopropyl methyl ketone, and otherwise the same procedure is followed, 5-[2'(3'',5''-di-tert.-butyl-4''-hydroxy-phenyl)-isopropyl]-5-methyl-hydantoin of melting point 240°C is obtained (stabiliser No. 3).

EXAMPLE 4

If, in Example 1, 3,5-di-tert.-butyl-4-hydroxyphenylethyl methyl ketone is replaced by an equivalent amount of 3,5-di-tert.-butyl-4-hydroxy-acetophenone, and otherwise the same procedure is followed, 5-(3',5'-di-tert.-butyl-4'-hydroxy-phenyl)-5-methyl-hydantoin of melting point 260°C is obtained (stabiliser No. 4).

EXAMPLE 5

If, in Example 1, 3,5-di-tert.-butyl-4-hydroxyphenylethyl methyl ketone is replaced by an equivalent amount of 3-(3',5'-di-tert.-butyl-4'-hydroxyphenyl)-propionaldehyde, and otherwise the same procedure is followed, 5-(3',5'-di-tert.-butyl-4'-hydroxy-phenylethyl)-hydantoin of melting point 207°–208°C is obtained (stabiliser No. 5).

EXAMPLE 6

If, in Example 1, 3,5-di-tert.-butyl-4-hydroxyphenylethyl -methyl ketone is replaced by an equivalent amount of 3-tert.-butyl-4-hydroxy-phenylethyl methyl ketone, and otherwise the same procedure is followed, 5-(3'-tert.-butyl-4'-hydroxy-phenylethyl)-5-methyl-hydantoin of melting point 246°C is obtained (stabiliser No. 6).

EXAMPLE 7

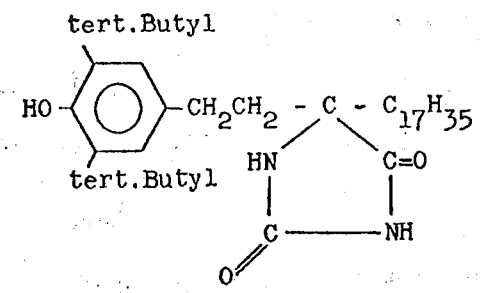

19.3 g (0.039 mol) of 3,5-di-tert.-butyl-4-hydroxyphenylethyl heptadecyl ketone, 1.9 g (0.039 mol) of sodium cyanide and 11.1 g (0.116 mol) of ammonium carbonate are initially introduced into 150 ml of 90% strength ethanol and the mixture is kept for 36 hours at 40°–45°C, whilst stirring. Thereafter, 150 ml of water are added to the pasty reaction mixture, which is stirred for a further hour at room temperature. After filtration, washing with water and then with hexane, and subsequent recrystallisation from hexane, 5-(3',5'-di-tert.-butyl-4'-hydroxy-phenylethyl)-5-heptadecyl-hydantoin (stabiliser No. 7) melts at 89°C.

EXAMPLE 8

If, in Example 7, 3,5-di-tert.-butyl-4-hydroxyphenylethyl heptadecyl ketone is replaced by an equivalent amount of di-(3,5-di-tert.-butyl-4-hydroxyphenylethyl) ketone of German Offenlegungsschrift No. 2,009,504 and otherwise the same procedure is followed, 5,5-bis-(3',5'-di-tert.-butyl-4'-hydroxyphenylethyl)-hydantoin (stabiliser No. 8) is obtained. Melting point 218°–220°C.

EXAMPLE 9

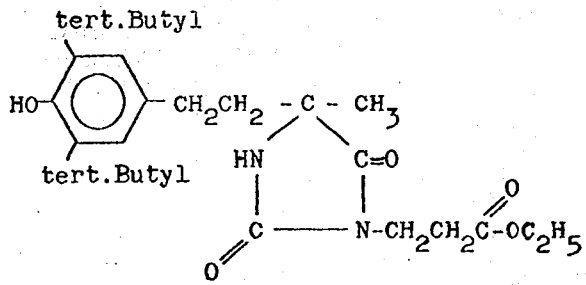

30 g (0.087 mol) of 5-(3',5'-di-tert.-butyl-4'-hydroxyphenylethyl)-5-methyl-hydantoin and 13.1 g (0.131 mol) of acrylic acid ethyl ester are dissolved in 100 ml of ethanol, 2 ml of a 40% strength solution of benzyl-trimethyl-ammonium hydroxide in methanol are added and the mixture is heated under reflux for 12 hours, whilst stirring. Thereafter it is neutralised with glacial acetic acid, diluted with 50 ml of water and cooled whilst stirring. The precipitate formed is filtered off, washed with 50% strength ethanol and recrystallised from 70% strength alcohol. 29 g of 5-(3',5'-di-tert.-butyl-4'-hydroxy-phenylethyl)-5-methyl-3-ethoxycarbonylethyl-hydantoin of melting point 100°C are thus obtained. (Stabiliser No. 9).

EXAMPLE 10

If, in Example 9, the acrylic acid ethyl ester is replaced by an equivalent amount of acrylonitrile and otherwise the same procedure is followed, 5-(3',5'-di-tert.-butyl-4'-hydroxy-phenylethyl)-5-methyl-3-cyanoethyl-hydantoin is obtained in the form of a light-colored resin (stabiliser No. 10).

EXAMPLE 11

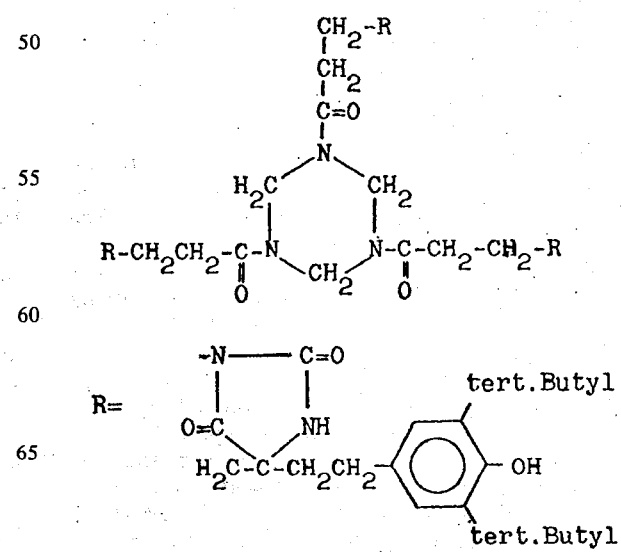

21 g (0.06 mol) of 5-(3',5'-di-tert.-butyl-4'-hydroxyphenylethyl)-5-methyl-hydantoin and 5 g (0.02 mol) of 1,3,5-tris-acryloyl-hexahydro-s-triazine are dissolved in 100 ml of dimethylformamide, a few drops of a concentrated sodium ethylate solution are added and the mixture is heated to 100°C over the course of 90 minutes, whilst stirring. The mixture is stirred for a further 5 hours at this temperature, the brownish solution is subsequently decolorised with a little glacial acetic acid, cooled and mixed first with toluene and then with 200 ml of water, and the organic phase which separates out is separated off. After thorough washing with water, the toluene phase is completely concentrated under reduced pressure. 1,3,5-tris-[5'-(3'',5''-Di-tert.-butyl-4''-hydroxy-phenylethyl)-5'-methyl-hydantoin-3'-yl]-propionylhexahydro-s-triazine, a light-colored brittle resin of softening point > 100°C is thus obtained. (Stabiliser No. 11)

EXAMPLE 12

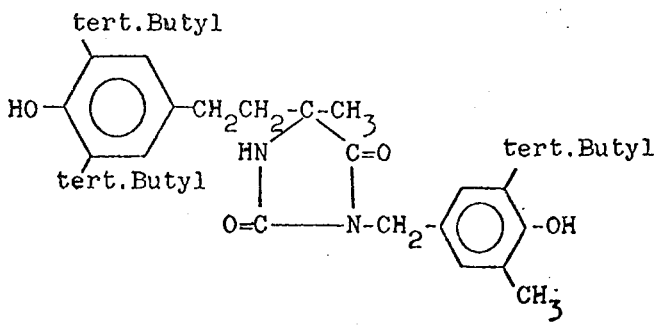

17.3 g (0.05 mol) of 5-(3',5'-di-tert.-butyl-4'-hydroxy-phenylethyl)-5-methyl-hydantoin and 11 g (0.05 mol) of (3-tert.-butyl-4-hydroxy-5-methyl-benzyl)dimethylamine are dissolved in 100 ml of dimethylformamide, a pinch of lithium amide is added and the mixture is heated to 90°C for 16 hours whilst stirring and passing nitrogen through it. The brown solution is brightened with a little glacial acetic acid and the solvent is distilled off under reduced pressure. On recrystallisation from acetonitrile, 20 g of 3-(3'-tert.-butyl-4'-hydroxy-5'-methyl-benzyl)-5-(3'',5''-di-tert.-butyl-4''-hydroxy-phenylethyl)-5-methyl-hydantoin of melting point 218°C (stabiliser No. 12) are obtained.

EXAMPLE 13

If, in Example 12, 5-(3',5'-di-tert.-butyl-4'-hydroxyphenylethyl)-5-methyl-hydantoin is replaced by an equivalent amount of 5-(3'-tert.-butyl-4'-hydroxy-5'-methyl-phenylethyl)-5-methyl-hydantoin and otherwise the same procedure is followed, 3-(3'-tert.-butyl-4'-hydroxy-5'-methyl-benzyl)-5-(3''-tert.-butyl-4''-hydroxy-5''-methyl-phenylethyl)-5-methyl-hydantoin of melting point 110°–120°C (stabiliser No. 13) is obtained.

EXAMPLE 14

If, in Example 12, 5-(3',5'-di-tert.-butyl-4'-hydroxyphenylethyl)-5-methyl-hydantoin is replaced by an equivalent amount of 5,5-bis-(3',5'-di-tert.-butyl-4'-hydroxy-phenylethyl)-hydantoin and otherwise the same procedure is followed, 5,5-bis-(3',5'-di-tert.-butyl-4'-hydroxy-phenylethyl)-3-(3''-tert.-butyl-4''-hydroxy-5''-methylbenzyl)-hydantoin of melting point 125°–130°C is obtained (stabiliser No. 14).

EXAMPLE 15

If, in Example 12, 5-(3',5'-di-tert.-butyl-4'-hydroxyphenylethyl)-5-methyl-hydantoin is replaced by an equivalent amount of 5-[2'-(3'',5''-di-tert.-butyl-4''-hydroxyphenyl)-isopropyl]-5-methyl-hydantoin and otherwise the same procedure is followed, 3-(3'-tert.-butyl-4'-hydroxy-5'-methylbenzyl)-5-[2-(3'',5''-di-tert.-butyl-4''-hydroxyphenyl)-isopropyl]-5-methyl-hydantoin of melting point 193°C is obtained (stabiliser No. 15).

EXAMPLE 16

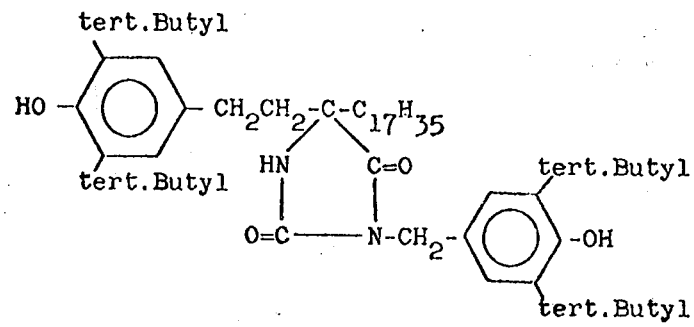

5.7 g (0.01 mol) of 5-(3',5'-di-tert.-butyl-4'-hydroxyphenylethyl)-5-heptadecyl-hydantoin and 2.6 g (0.01 mol) of (3,5-di-tert.-butyl-4-hydroxybenzyl)dimethylamine are dissolved in 50 ml of dimethylformamide and the mixture is stirred for 16 hours at 100°C whilst passing nitrogen through it. The brown solution is brightened with a little glacial acetic acid and the solvent is distilled off under reduced pressure. On recrystallisation from acetonitrile, 3-(3',5'-di-tert.-butyl-4'-hydroxybenzyl)-5-(3'',5''-di-tert.-butyl-4''-hydroxy-phenylethyl)-5-heptadecyl-hydantoin melts at 48°–50°C (stabiliser No. 16).

EXAMPLE 17

If, in Example 16, 5-(3',5'-di-tert.-butyl-4'-hydroxyphenylethyl)-5-heptadecyl-hydantoin is replaced by an equivalent amount of 5-(3',5'-di-tert.-butyl-4'-hydroxy-phenylethyl)-5-methyl-hydantoin and otherwise the same procedure is followed, 3-(3',5'-di-tert.-butyl-4'-hydroxybenzyl)-5-(3'',5''-di-tert.-butyl-4''-hydroxyphenylethyl) -5-methyl-hydantoin of melting point 217°C (stabiliser No. 17) is obtained.

EXAMPLE 18

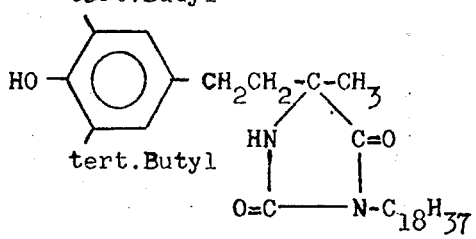

12.1 g (0.035 mol) of 5-(3',5'-di-tert.-butyl-4'-hydroxy-phenylethyl)-5-methyl-hydantoin, 11.65 g (0.035 mol) of 1-bromooctadecane and 1.9 g (0.035 mol) of sodium methylate (dissolved in 10 ml of methanol) are initially introduced into 100 ml of dimethylformamide and the mixture is stirred for 14 hours at 80°C. Thereafter it is cooled, first mixed with 100 ml of toluene and then with 100 ml of water, and the organic phase is separated off. After thorough washing with water, the toluene phase is completely concentrated under reduced pressure and taken up in acetonitrile. After prolonged standing, 15 g of 5-(3',5'-di-tert.-butyl-4'-hydroxyphenylethyl)-5-methyl-3-octadecyl-hydantoin of melting point 62°C (stabiliser No. 18) crystallise.

EXAMPLE 19

If, in Example 18, the 1-bromooctadecane is replaced by an equivalent amount of 1-bromohexadecane and otherwise the same procedure is followed, 5-(3',5'-di-tert.-butyl-4'-hydroxy-phenylethyl)-5-methyl-3-hexadecyl-hydantoin of melting point 64°C (stabiliser No. 19) is obtained.

EXAMPLE 20

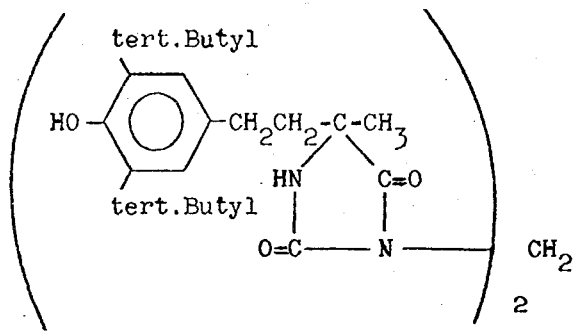

34.6 g (0.1 mol) of 5-(3',5'-di-tert.-butyl-4'-hydroxy-phenylethyl)-5-methyl-hydantoin, 8.7 g (0.05 mol) of methylene bromide and 38 g (0.1 mol) of potassium hydroxide are initially introduced into 100 ml of dimethylformamide and the mixture is kept at 80°C for 16 hours, whilst stirring. After cooling, insoluble matter is filtered off, first 100 ml of toluene and then 100 ml of water are added and the toluene phase is separated off and repeatedly washed with water. Thereafter, 50 ml of toluene are distilled off under reduced pressure and the residual brown solution is left to stand for 24 hours at room temperature. The resulting precipitate is filtered off and recrystallised from acetonitrile. 3,3'-methylene-bis[5-(3'',5''-di-tert.-butyl-4''-hydroxy-phenylethyl)-5-methyl-hydantoin] of melting point 222°C (stabiliser No. 20) are thus obtained.

EXAMPLE 21

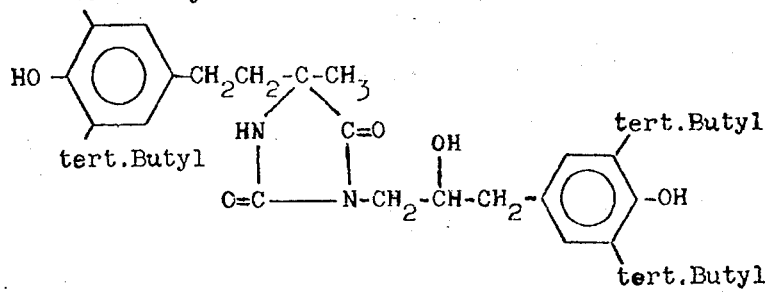

17.3 g (0.05 mol) of 5-(3',5'-di-tert.-butyl-4'-hydroxy-phenylethyl)-5-methyl-hydantoin, 13 g (0.05 mol) of (3,5-di-tert.-butyl-4-hydroxybenzyl)-oxirane and 1 g of tripropylamine in 100 ml of dimethylformamide are heated for 5 hours under reflux, whilst stirring. After cooling, 5 ml of glacial acetic acid, 100 ml of toluene and 100 ml of water are added. The toluene phase is washed with water, completely concentrated under reduced pressure and dissolved in acetonitrile to give a concentrated solution. After prolonged standing, a precipitate forms and is filtered off. 3-[3'-(3'',5''-di-tert.-butyl-4''-hydroxyphenyl)-2-hydroxy]-propyl-5-(3''',5'''-di-tert.-butyl-4'''-hydroxy-phenylethyl)-5-methylhydantoin of melting point 193°C (stabiliser No. 21) is thus obtained.

EXAMPLE 22

6.95 g (0.02 mol) of 5-(3'5'-di-tert-butyl-4'-hydroxy-phenylethyl)-5-methylhydantoin, 1.4 g (0.01 mol) of potassium carbonate and 1.55 g (0.01 mol) of 1,6-dichlorohexane in 30 ml of dimethylformamide are stirred for 20 hours at 100°C under nitrogen. After cooling, the mixture is added slowly to 120 ml of water with stirring. The precipitated solid is removed by filtration, dried and dissolved in 40 ml of ethanol and decolorized with charcoal. The ethanol solution is filtered and the filtrate added to 400 ml of water with stirring to yield a thick, white suspension which is then filtered. 3,3'-Hexamethylene-bis [5(3'',5''-di-tert-butyl-4''-hydroxyphenylethyl)-5-methylhydantoin] is thus obtained as a white solid of melting point 100°–112°C. (stabiliser No. 22).

EXAMPLE 23

If, in Example 22, the 1,6-dichlorohexane is replaced by an equivalent amount of bis(2-chloroethyl)ether and otherwise the same procedure is followed, 3,3'- oxydiethylene-bis [ 5-(3'',5''-di-tert-butyl-4''-hydroxyphenylethyl)-5-methylhydantoin] of melting point 105°–106°C is obtained (stabiliser No. 23).

EXAMPLE 24

5.65 g (0.01 mol) of 3-(3',5'-di-tert-butyl-4'-hydroxybenzyl)-5-(3'',5''-di-tert-butyl-4''-hydroxyphenylethyl)-5-methylhydantoin and 4.35 g (0.02 mol) of (3,5-di-tert-butyl-4-hydroxybenzyl)dimethylamine are dissolved in 20 ml of dimethylformamide and stirred under nitrogen for 44 hours at 120°C. The reaction mixture is cooled and poured slowly into 120 ml of water with stirring. The product is isolated from this mixture by successive extractions with 100 ml and then two 75 ml portions of benzene. The combined benzene extracts are dried and completely concentrated under reduced pressure. The residue is taken up in 100 ml of hot heptane and after cooling, the insoluble crystals are removed by filtration. The filtrate is evaporated to dryness under reduced pressure, and the residue again dissolved in 100 ml of benzene. The benzene solution is washed successively with two 40 ml portions of 3N hydrochloric acid and one 40 ml portion of water. The dried benzene solution is again completely concentrated under reduced pressure. The residue is taken up in boiling hexane, and an insoluble fraction is separated by filtration. The filtrate is evaporated to dryness under reduced pressure. After recrystallization from petroleum ether, 1,3-di(3',5',-di-tert-butyl-4'-hydroxybenzyl)-5-(3'',5''-di-tert-butyl-4''-hydroxyphenylethyl)-5-methylhydantoin of melting point 112°–114°C is obtained. (stabiliser No. 24).

EXAMPLE 25

7.75 g (0.01 mol) of 3,3'-hexamethylene-bis-[5-(3'',5''-di-tert-butyl-4''-hydroxyphenylethyl)-5-methylhydantoin] is added portionwise with stirring to a slurry of 1.92 g (0.04 mol) of a 50% dispersion of sodium hydride in mineral oil in 100 g of dry dimethylformamide. The temperature of the reaction mixture is maintained at 50°–55°C until gas evolution ceases. 3.3 g (0.02 mol) of 1-bromohexane is then added dropwise over a period of 15–30 minutes. The temperature of the mixture is maintained between 60°–80°C until the reaction is complete. The reaction mixture is then poured into water and neutralized with dilute hydrochloric acid. The mixture is then extracted with chloroform. The chloroform phase is dried and completely concentrated under reduced pressure to yield as the residue the desired 3,3'-hexamethylene-bis[5-(3'',5''-di-tert-butyl-4''-hydroxyphenylethyl)-5-methyl-1-n-hexylhydantoin].

EXAMPLE 26

5-(3',5'-di-tert-butyl-4'-hydroxyphenylethyl)hydantoin is treated with morpholine and formaldehyde according to the procedure of O. O Orazi and R. A. Corral, *Tetrahedron*, 15, 93 (1961) to prepare the corresponding 3-N-morpholinomethyl-5-(3',5'-di-tert-butyl-4'-hydroxyphenylethyl)hydantoin. This material is then alkylated in the 1-position with 1-bromohexane as described in Example 25. The morpholinomethyl group is removed by subsequent hydrolysis according to the procedure of O. O. Orazi and R. A. Corral, *Experientia*, 21, 508 (1965) to give 5-(3',5'-di-tert-butyl-4'-hydroxyphenylethyl)-1-n-hexylhydantoin.

EXAMPLE 27

7.8 g (0.12 mole) of potassium cyanide in 40 ml of water is slowly added to a stirred solution of 27.6 g (0.1 mole) of 3,5-di-tert-butyl-4-hydroxyphenylethyl methyl ketone and 27.0 g (0.1 mole) of n-octadecylamine in 200 ml of glacial acetic acid at 15°–25°C. The mixture is stirred at 20°–25°C for 3.5 hours after addition is complete and then allowed to stand overnight at room temperature. The reaction mixture is then diluted with water and extracted with ether. The ether extract is dried and evaporated to dryness. The crude aminonitrile thus obtained is dissolved in 200 ml of glacial acetic acid containing 10 ml of concentrated hydrochloric acid and reacted with 16.2 g (0.2 mole) of potassium cyanate in 50 ml of water. The reaction mixture is warmed at 35°–50°C for 3 hours, then cooled and poured into water. The solid obtained is removed by filtration and then refluxed with 300 ml of 20% aqueous hydrochloric acid for 30 minutes. The solution is cooled and the desired product, 5-(3',5'-di-tert-butyl-4'-hydroxyphenylethyl)-5-methyl-1-n-octadecylhydantoin, is isolated by filtration, washed, dried and recrystallized.

EXAMPLE 28

If, in Example 16, 5-(3',5'-di-tert-butyl-4'-hydroxyphenylethyl)-5-heptadecylhydantoin is replaced by an equivalent amount of 5-(3',5', -di-tert-butyl-4'-hydroxyphenylethyl)-5-methyl-1-n-octadecylhydantoin and otherwise the same procedure is followed, 3-(3',5'-di-tert-butyl-4'-hydroxybenzyl)-5-(3'',5''-di-tertbutyl-4''-hydroxyphenylethyl)-5-methyl-1-n-octadecylhydantoin is obtained.

EXAMPLE 29

100 parts of polypropylene (melt index 3.2 g/10 minutes, 230°C/2,160 g) are thoroughly mixed for 10 minutes in a shaking apparatus, with 0.2 part of an additive listed in Table 1 below.

The resulting mixture is kneaded for 10 minutes in a Brabender plastograph at 200°C and the mass thus obtained is subsequently pressed in a sheet press at 260°C platen temperature to give 1 mm thick sheets, from which strips 1 cm wide and 17 cm long are punched.

The activity of the additives introduced into the test strips is tested by heat aging in a circulating air oven at 149°C, using, for comparison, an additive-free test strip. 3 test strips of each formulation are employed. The incipient, easily visible decomposition of the test strip is defined as the end point. The results are quoted in days.

Table 1

| Stabiliser No. | Days to incipient decomposition 149°C |
|---|---|
| No additive | ½ |
| 7 | 10 |
| 12 | 7 |
| 13 | 15 |
| 16 | 17 |
| 17 | 6 |
| 18 | 10 |
| 21 | 19 |

EXAMPLE 30

The test specimens described in Example 29 were additionally tested for their color stability, namely:
a. after incorporation (Table 2, column 2).
b. after 500 hours' exposure in a Xenotest instrument of Messrs. Hanau (Table 2, column 3)
c. after 1 week's treatment with boiling water (Table 2, column 4).

An empirical color scale was used for Table 2, in which 5 denotes colorless, 4 denotes a just perceptible slight discoloration and 3, 2, 1 and < 1 denote progressively stronger discoloration.

Table 2

| Stabiliser No. | Colour assessment according to scale 1 to 5 | | |
|---|---|---|---|
| | After incorporation | After exposure to light | Boiling water, 1 week |
| 2 | 4 | 4 | 5 |
| 7 | 4–5 | 5 | 4 |
| 12 | 4–5 | 5 | 4–5 |
| 13 | 4–5 | 4–5 | 4–5 |
| 16 | 4–5 | 5 | 4–5 |
| 17 | 4–5 | 5 | 4–5 |
| 18 | 4–5 | 5 | 5 |
| 21 | 4–5 | 5 | 4–5 |

EXAMPLE 31

100 parts of polypropylene (melt index 3.2 g/10 minutes, 230°C/2,160 g) are thoroughly mixed for 10 minutes in a shaking apparatus with 0.1 part of an additive listed in Table 3 below and 0.3 part of dilauryl thiodipropionate.

The resulting mixture is kneaded for 10 minutes in a Brabender plastograph at 200°C and the mass thus obtained is subsequently pressed in a sheet press at 260°C platen temperature to give 1 mm thick sheets from which strips 1 cm wide and 17 cm long are punched.

The activity of the additives introduced into the pressed strips is tested by heat aging in a circulating air oven at 149°C. using for comparison a test strip which only contains 0.3 part of dilauryl thiodipropionate. Three test strips of each formulation are employed. The incipient, easily visible decomposition of the test strip is defined as the end point and the results are quoted in days.

Table 3

| Stabiliser No. | Days up to incipient decomposition 149°C |
|---|---|
| No additive | 5 |
| 7 | 24 |
| 12 | 19 |
| 13 | 17 |
| 16 | 40 |
| 17 | 14 |
| 18 | 21 |
| 21 | 32 |

EXAMPLE 32

The test specimens described in Example 31 were additionally tested for their color stability, namely:
a. after incorporation (Table 4, column 2).
b. after 500 hours' exposure in a Xenotest instrument of Messrs. Hanau (Table 4, column 3)
c. after 1 week's treatment with boiling water (Table 4, column 4).

An empirical color scale was used for Table 4, in which 5 denotes colorless, 4 denotes a just perceptible slight discoloration and 3, 2, 1 and <1 denote progressively stronger discoloration.

Table 4

| Stabiliser No. | Colour assessment according to scale 1 to 5 | | |
|---|---|---|---|
| | After incorporation | After exposure to light | Boiling water, 1 week |
| 2 | 4 | 4 | 5 |
| 7 | 4–5 | 5 | 4 |
| 12 | 5 | 5 | 5 |
| 13 | 5 | 5 | 5 |
| 16 | 4–5 | 5 | 5 |
| 17 | 4–5 | 5 | 4–5 |
| 18 | 5 | 5 | 5 |
| 21 | 4–5 | 5 | 4–5 |

EXAMPLE 33

Shavings (chips) of 25μ thickness are cut by means of a microtome from the 1 mm thick test sheets described in Example 29. These chips are sandwiched between stainless steel grids and the sample carriers thus obtained are suspended in a circulating air oven and the samples are aged at 135°C and 147°C, respectively.

The time after which, on gentle tapping on the grid, degraded polypropylene falls out in the form of a powder is defined as the end point (a check is made 1 – 2x daily). The results are quoted in hours. (Table 5).

Table 5

| Stabiliser No. | Hours to incipient decomposition | |
|---|---|---|
| | 147°C | 135°C |
| No additive | 10 | 20 |
| 7 | 40 | 140 |
| 16 | 70 | 220 |
| 21 | 140 | 380 |

EXAMPLE 34

Shavings (chips) of 25μ thickness are cut by means of a microtome from the 1 mm thick test sheets described in Example 31. These chips are clamped between stainless steel grids and the sample carriers thus obtained are suspended in a circulating air oven and the samples are aged at 135°C or 147°C. The time after which, on gentle tapping on the grid, degraded polypropylene falls out in the form of a powder is defined as the end point (a check is made 1 – 2x daily). The results are quoted in hours. (Table 6).

Table 6

| Stabiliser No. | Hours to incipient decomposition | |
|---|---|---|
| | 147°C | 135°C |
| No additive | 10 | 20 |
| 7 | 70 | 220 |
| 16 | 210 | 550 |
| 21 | 140 | 380 |

EXAMPLE 35

A batch of unstabilized polypropylene powder (Hercules Profax 6501) is thoroughly blended with 0.2% by weight of various compounds of this invention. The blended materials are then milled on a two-roll mill at 182°C for 5 minutes after which time the stabilized polypropylene is sheeted from the mill and allowed to cool.

The milled polypropylene sheets are then cut into pieces and pressed for 5 minutes on a hydraulic press at 218°C and 275 pounds per square inch pressure. The resulting sheet of 25 mil thickness is tested for resistance to accelerated aging in a forced draft oven at 150°C. The results are set out in Table 7.

Table 7

| Stabilizer No. | Oven Aging at 150°C Hours to Failure |
|---|---|
| 17 | 90 |
| 22 | 330 |
| 23 | 260 |
| 24 | 250 |
| Unstabilized Polypropylene | 3 |

EXAMPLE 36

Test specimens are prepared exactly as described in Example 35 except that the stabilized polypropylene contains 0.2% by weight of various compounds of this invention and 0.5% by weight of 5-chloro-2-(2'-hydroxy-3',5'-di-tert-butylphenyl) benzotriazole as a co-stabilizer. Results of accelerated aging tests in a forced draft oven at 150°C are shown in Table 8.

Table 8

| Stabiliser No. (Plus Co-Stabiliser) | Oven Aging at 150°C Hours to Failure |
|---|---|
| 17 | 80 |
| 22 | 105 |
| 23 | 165 |
| 24 | 250 |
| Unstabilized Polypropylene | 3 |

EXAMPLE 37

Test specimens are prepared exactly as described in Example 35 except that the stabilized polypropylene contains 0.1% by weight of various compounds of this invention and 0.3% by weight of distearyl thiodipropionate as a co-stabiliser. Results of accelerated aging tests in a forced draft oven at 150°C are shown in Table 9.

Table 9

| Stabiliser No. (Plus Co-Stabiliser) | Oven Aging at 150°C Hours to Failure |
|---|---|
| 17 | 430 |
| 22 | 870 |
| 23 | 690 |
| 24 | 1645 |
| Unstabilised Polypropylene | 3 |
| With Co-Stabiliser Only | 100 |

EXAMPLE 38

Test specimens are prepared exactly as those described in Example 36 except that the milled polypropylene sheets are cut into pieces and pressed for 3 minutes on a hydraulic press at 218°C and 275 pounds per square inch pressure. The resulting sheet of 5 mil thickness is tested in fluorescent sunlight black light environment with the development of carbonyl absorption in the infrared spectrum at the 585 millimicron wavelength being the measure of stabilsation protection afforded by the stabilisers present in the polypropylene. Failure is taken as the hours required to cause the carbonyl absorption to reach a value of 0.5. Such a value correlates with the reduction of physical properties of the polypropylene pellicle to unacceptable levels. The results are set out in Table 10.

Table 10

| Stabiliser No. (Plus Co-Stabiliser) | Fluorescent Sunlight Black Light Test Hours to Failure (0.5 Carbonyl Absorption) |
|---|---|
| 17 | 820 |
| 22 | 765 |
| 23 | 590 |
| 24 | 980 |
| Unstabilised Polypropylene | 225 |

What is claimed is:

1. A compound of the formula

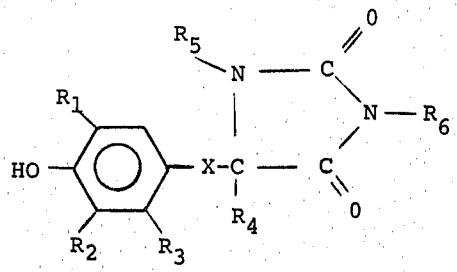

wherein $R_1$ denotes alkyl with 1 to 8 carbon atoms, cycloalkyl with 6 to 8 carbon atoms or aralkyl with 7 to 9 carbon atoms; $R_2$ denotes hydrogen, alkyl with 1 to 8 carbon atoms, cycloalkyl with 6 to 8 carbon atoms or aralkyl with 7 to 9 carbon atoms; $R_3$ denotes hydrogen or methyl; X denotes a direct bond, alkylene with 1 to 18 carbon atoms, which can be interrupted by oxygen or sulphur atoms, or the radical —OCH$_2$— wherein the oxygen atom is bonded to the phenol radical; $R_4$ denotes hydrogen, alkyl with 1 to 17 carbon atoms, alkenyl with 2 to 17 carbon atoms, thiaalkyl with 3 to 21 carbon atoms, oxaalkyl with 3 to 21 carbon atoms, cyclohexyl, benzyl, phenyl, alkylphenyl with 7 to 14 carbon atoms, alkoxyphenyl with 7 to 24 carbon atoms, chlorophenyl, dichlorophenyl, naphthyl or a group

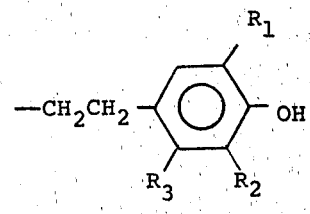

or X and $R_4$ conjointly with the carbon atom in the 5-position of the hydantoin ring denote one of the radicals

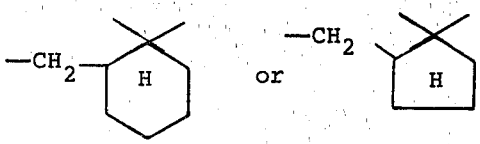

$R_5$ denotes hydrogen, alkyl with 1 to 18 carbon atoms, alkenyl with 3 to 18 carbon atoms, cyclohexyl, benzyl or hydroxybenzyl which is unsubstituted or substituted by 1 to 3 alkyl groups each with 1 to 4 carbon atoms; $R_6$ denotes alkenyl with 3 to 18 carbon atoms, cyclohexyl, benzyl or hydroxybenzyl which is unsubstituted or substituted by 1 to 3 alkyl groups each with 1 to 4 carbon atoms.

2. A compound according to claim 1 wherein $R_1$ denotes alkyl with 1 to 4 carbon atoms or cycloalkyl with 6 to 8 carbon atoms; $R_2$ denotes hydrogen, alkyl with 1 to 4 carbon atoms or cycloalkyl with 6 to 8 carbon atoms; $R_3$ denotes hydrogen; X denotes one of the radicals —CH$_2$CH$_2$— or

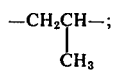

$R_4$ denotes alkyl with 1 to 17 carbon atoms, cyclohexyl, benzyl, phenyl or a group

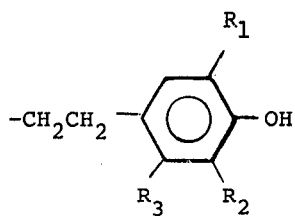

$R_5$ denotes hydrogen, alkyl with 1 to 18 carbon atoms or hydroxybenzyl substituted by 1 to 3 alkyl groups each having 1 to 4 carbon atoms; $R_6$ denotes hydroxybenzyl substituted by 1 to 3 alkyl groups each having 1 to 4 carbon atoms.

3. A compound according to claim 1, of the formula

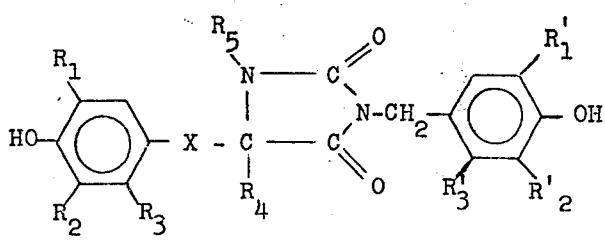

wherein $R_1$, $R_2$, $R_1'$ and $R_2$ independently of one another denote alkyl with 1 to 4 carbon atoms; $R_3$ and $R_3'$ independently of one another denote hydrogen or methyl, X denotes a direct bond, —CH$_2$—CH$_2$— or

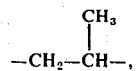

$R_4$ denotes alkyl with 1 to 17 carbon atoms, cyclohexyl, benzyl, phenyl or a group

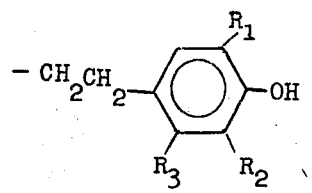

and $R_5$ denotes hydrogen or hydroxybenzyl substituted by 1 to 3 alkyl groups each having 1 to 4 carbon atoms.

4. A compound according to claim 1 which is 3-(3'-tert-butyl-4'-hydroxy-5'-methylbenzyl)-5-(3'',5''-di-tert-butyl-4''-hydroxyphenylethyl)-5-methylhydantoin.

5. A compound according to claim 1 which is 3-(3'-tert-butyl-4'-hydroxy-5'-methylbenzyl)-5-(3''-tert-butyl-4''-hydroxy-5''-methylphenylethyl)-5-methylhydantoin.

6. A compound according to claim 1 which is 3-(3',5'-di-tert-butyl-4'-hydroxybenzyl)-5-(3'',5''-di-tert-butyl-4''-hydroxyphenylethyl)-5-heptadecylhydantoin.

7. A compound according to claim 1 which is 3-(3',5'-di-tert-butyl-4'-hydroxybenzyl)-5-(3'',5''-di-tert butyl-4''-hydroxyphenylethyl)-5-methylhydantoin.

8. A compound according to claim 1 which is 1,3-di(3',5'-di-tert-butyl-4'-hydroxybenzyl)-5-(3'',5''-di-tert-butyl-4''-hydroxyphenylethyl)-5-methylhydantoin.

* * * * *